(12) United States Patent
Byerly et al.

(10) Patent No.: US 12,171,989 B2
(45) Date of Patent: *Dec. 24, 2024

(54) MEDICATION DELIVERY DEVICE

(71) Applicant: Eli Lilly and Company, Indianapolis, IN (US)

(72) Inventors: Roy Howard Byerly, Indianapolis, IN (US); Collin Hunter Grimes, Halethorpe, MD (US); Jeffrey Manfred Gunnarsson, Baltimore, MD (US); Chenrong Meng, Shanghai (CN); Andre Rafael Minoli, Baltimore, MD (US); Mariano Mumpower, Baltimore, MD (US); Brian Gregory Murphy, Baltimore, MD (US); Aaron Samuel Pearl, Baltimore, MD (US); Abbie Lynn Shoemaker, Baltimore, MD (US); Samuel Robert Zschack, Baltimore, MD (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 15 days.

This patent is subject to a terminal disclaimer.

(21) Appl. No.: 17/947,574

(22) Filed: Sep. 19, 2022

(65) Prior Publication Data

US 2023/0017492 A1    Jan. 19, 2023

Related U.S. Application Data

(63) Continuation of application No. 16/631,567, filed as application No. PCT/US2018/046860 on Aug. 17, 2018, now Pat. No. 11,524,117.

(Continued)

(51) Int. Cl.
*A61M 5/315*    (2006.01)

(52) U.S. Cl.
CPC .... *A61M 5/31546* (2013.01); *A61M 5/31535* (2013.01); *A61M 5/31568* (2013.01);
(Continued)

(58) Field of Classification Search
CPC ...... A61M 2205/3327; A61M 2205/50; A61M 2205/3306; A61M 2205/52;
(Continued)

(56) References Cited

U.S. PATENT DOCUMENTS

| 6,585,698 B1 | 7/2003 | Packman et al. |
| 7,291,132 B2 | 11/2007 | DeRuntz et al. |

(Continued)

FOREIGN PATENT DOCUMENTS

| EP | 3058970 | 8/2016 |
| WO | 05004955 | 1/2005 |

(Continued)

OTHER PUBLICATIONS

Patent Cooperation Treaty International Search Report pertaining to International Application No. PCT/US2018/046860 filed Aug. 17, 2018; Date of Mailing: Nov. 9, 2018.

(Continued)

*Primary Examiner* — Tasnim Mehjabin Ahmed
(74) *Attorney, Agent, or Firm* — M. Daniel Spillman

(57) ABSTRACT

The present disclosure relates to a dose detection system for use in combination with a medication delivery device in which a dose setting member rotates relative to an actuator during dose delivery. The dose detection system includes a module which is removably attached to the medication delivery device. The module includes a dosing component attached to the actuator during dose delivery. The dosing component includes a light source and a light sensor. A sensed element is attached to the dose setting member and includes surface features detectable by the light sensor.

13 Claims, 8 Drawing Sheets

Related U.S. Application Data

(60) Provisional application No. 62/547,168, filed on Aug. 18, 2017.

(52) U.S. Cl.
CPC .......... *A61M 5/31585* (2013.01); *A61M 2005/31588* (2013.01); *A61M 2205/3306* (2013.01); *A61M 2205/3327* (2013.01); *A61M 2205/50* (2013.01)

(58) Field of Classification Search
CPC .... A61M 2005/31588; A61M 5/31528; A61M 5/31593; A61M 5/31585; A61M 5/31568; A61M 5/31535; A61M 5/31546
See application file for complete search history.

(56) References Cited

U.S. PATENT DOCUMENTS

| | | | |
|---|---|---|---|
| 8,197,449 B2 | 6/2012 | Nielsen et al. | |
| 9,623,188 B2 | 4/2017 | Nielsen et al. | |
| 11,524,117 B2 * | 12/2022 | Byerly | A61M 5/20 |
| 2013/0197445 A1 | 8/2013 | Schabbach et al. | |
| 2014/0039396 A1 | 2/2014 | Geipel et al. | |
| 2014/0194829 A1 | 7/2014 | Baek et al. | |
| 2015/0202375 A1 | 7/2015 | Schabbach et al. | |
| 2016/0030680 A1 | 2/2016 | Veasey et al. | |
| 2016/0082192 A1 | 3/2016 | Veasey et al. | |
| 2016/0303326 A1 | 10/2016 | Binier | |
| 2018/0008778 A1 * | 1/2018 | Erbstein | A61M 5/3155 |
| 2018/0154086 A1 * | 6/2018 | Toporek | A61M 5/31551 |
| 2020/0197614 A1 | 6/2020 | Erbstein et al. | |

FOREIGN PATENT DOCUMENTS

| | | |
|---|---|---|
| WO | 2014180744 | 11/2014 |
| WO | 2015103784 | 7/2015 |
| WO | 2015136513 | 9/2015 |
| WO | 2016142511 | 9/2016 |
| WO | 2016198516 | 12/2016 |
| WO | 2017097507 | 6/2017 |
| WO | 2018013419 | 1/2018 |
| WO | 2018046680 | 3/2018 |
| WO | 2018069183 | 4/2018 |
| WO | 2018104289 | 6/2018 |
| WO | 2018160425 | 9/2018 |

OTHER PUBLICATIONS

Patent Cooperation Treaty Written Opinion of the International Searching Authority pertaining to International Application No. PCT/US2018/046860 filed Aug. 17, 2018; Date of Mailing: Nov. 9, 2018.

* cited by examiner

MEDICATION DELIVERY DEVICE

TECHNICAL FIELD

The present disclosure relates to an electronic dose detection system for a medication delivery device, and illustratively to an electronic dose detection module adapted to removably attach to a proximal end portion of a medication delivery device. The dose delivery detection system is operable to detect the amount of a dose of medication delivered by the medication delivery device.

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device, and which detects the relative movement of a sensed component secured to a second member of the device.

The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event. Further, there is a need for such a dose detection device to be removable and reusable with multiple delivery devices.

SUMMARY

In accordance with an aspect of the present disclosure, a dose detection system is provided for a medication delivery device which includes a dose setting member which rotates relative to an actuator during dose delivery. The dose detection system comprises an electronics assembly attached to the actuator and a sensed element attached to the dose setting member. The electronics assembly includes a rotation sensor operable with the sensed element to detect the movement of the dose setting member relative to the actuator during dose delivery. The electronics assembly may further include various additional components such as one or more other sensors, memory, a processor, a controller, a battery, etc.

In another aspect, the dose delivery detection system comprises a module which is removably attachable to the medication delivery device. Among other advantages, the attachable and detachable module is operative to detect a delivered medication amount without changing the functionality or operation of the medication delivery device to which it is attached. In some embodiments, the sensing system records the size of the delivered dose and communicates the information to an external device. The medication delivery device may include a medication. Other advantages will be recognized by those of ordinary skill in the art.

BRIEF DESCRIPTION OF THE DRAWINGS

The features and advantages of the present disclosure will become more apparent to those skilled in the art upon consideration of the following detailed description taken in conjunction with the accompanying figures.

DETAILED DESCRIPTION

Figure 1:
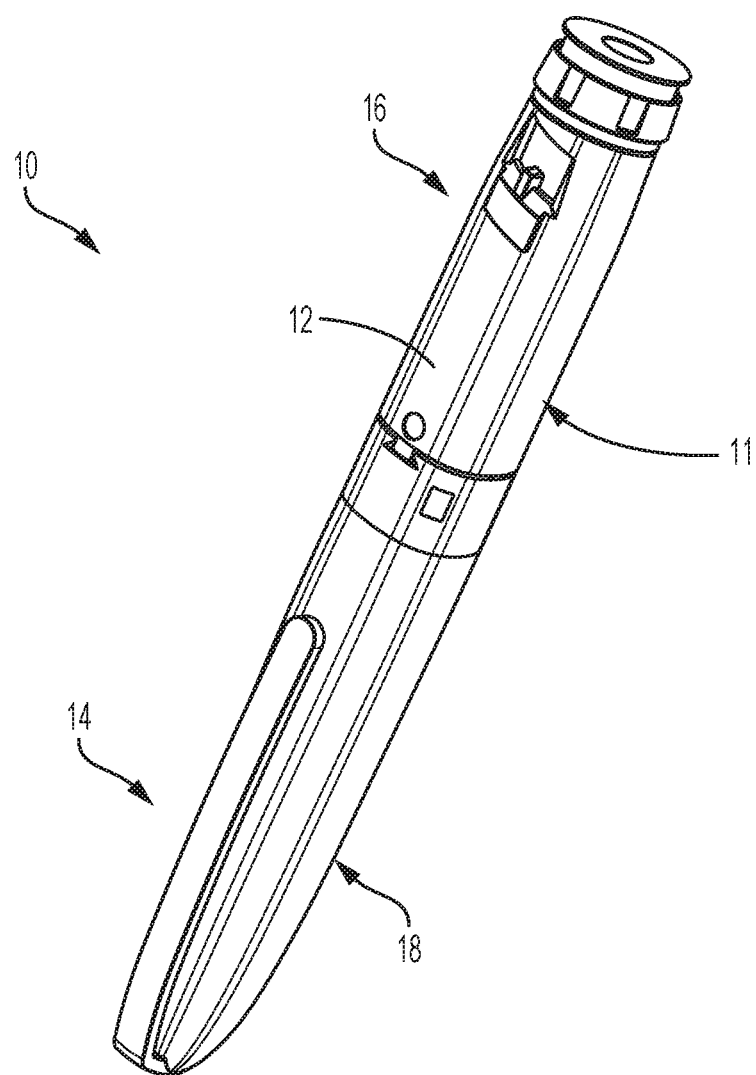
FIG. 1 is a perspective view of an exemplary medication delivery device with which the dose detection system of the present disclosure is operable.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for determining the amount of a dose delivered by a medication delivery device based on the sensing of relative rotational movement between a dose setting member and an actuator of the medication delivery device. The sensed relative rotational movements are correlated to the amount of the dose delivered. By way of illustration, the medication delivery device is described in the form of a pen injector. However, the medication delivery device may be any device which is used to set and to deliver a dose of a medication, such as a pen injector, an infusion pump or a syringe. The medication may be any of a type that may be delivered by such a medication delivery device.

Devices described herein, such as a device 10, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
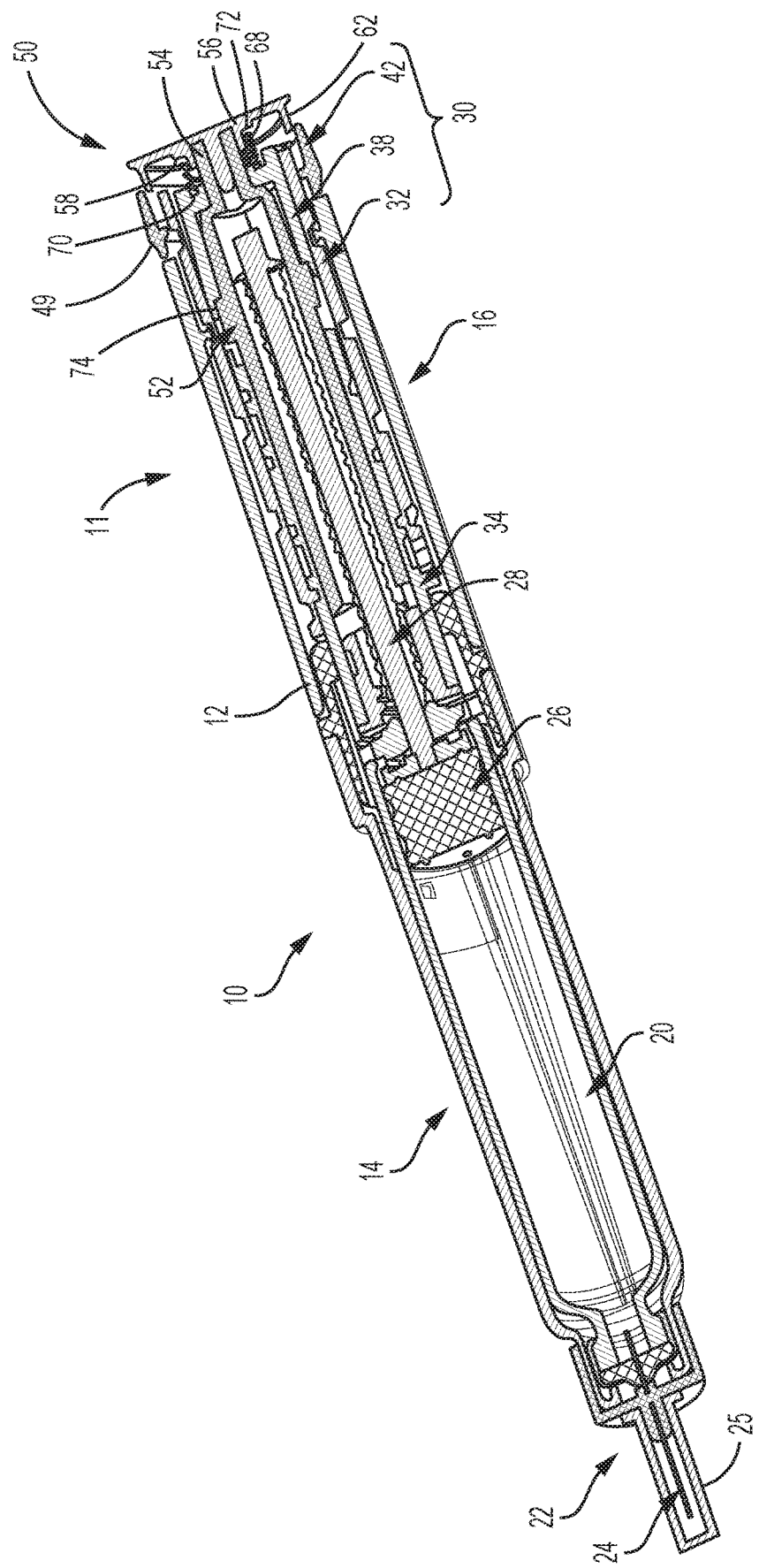
FIG. 2 is a cross-sectional perspective view of the exemplary medication delivery device of FIG. 1.

An exemplary medication delivery device 10 is illustrated in FIGS. 1-4 as a pen injector configured to inject a medication into a patient through a needle. Pen injector 10 includes a body 11 comprising an elongated, pen-shaped housing 12 including a distal portion 14 and a proximal portion 16. Distal portion 14 is received within a pen cap 18. Referring to FIG. 2, distal portion 14 contains a reservoir or cartridge 20 configured to hold the medicinal fluid to be dispensed through its distal outlet end during a dispensing operation. The outlet end of distal portion 14 is equipped with a removable needle assembly 22 including an injection needle 24 enclosed by a removable cover 25. A piston 26 is positioned in reservoir 20. An injecting mechanism positioned in proximal portion 16 is operative to advance piston 26 toward the outlet of reservoir 20 during the dose dispensing operation to force the contained medicine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (i.e., simultaneously move axially and rotationally) relative to housing 12 during dose setting and dose dispensing. FIGS. 1 and 2 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection.

Figures 3, 4:
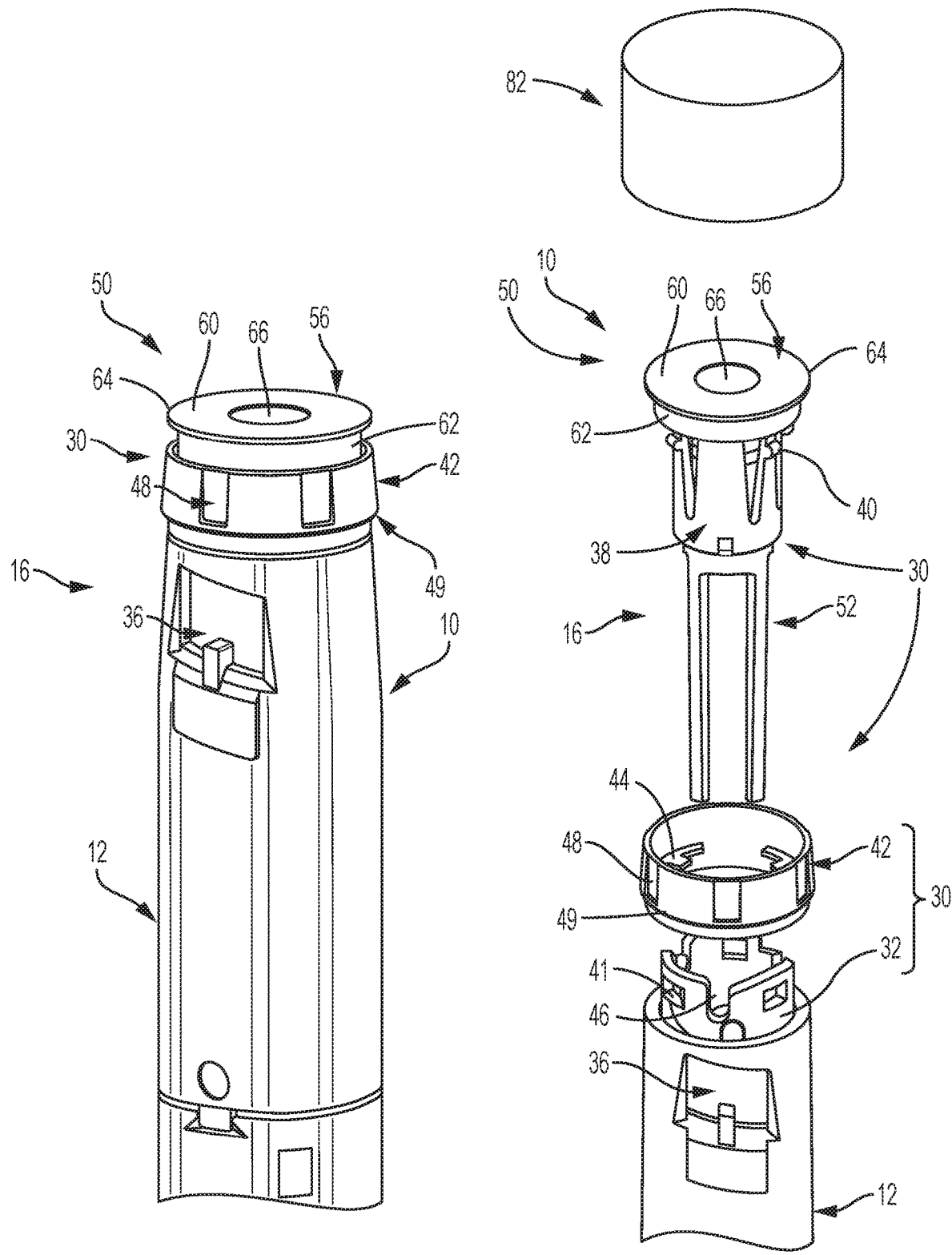
FIG. 3 is a perspective view of the proximal portion of the exemplary medication delivery device of FIG. 1.
FIG. 4 is a partially-exploded, perspective view of the proximal portion of the exemplary medication delivery device of FIG. 1, and showing a dose detection module.

Referring to FIGS. 2-4, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner surface that engages a threaded outer surface of sleeve 34 (FIG. 2) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dose dial member 32 by detents 40 received within openings 41 in dial member 32. Dose setting member 30 further includes a collar or skirt 42 positioned around the outer periphery of dial member 32 at its proximal end. Skirt 42 is axially and rotationally locked to dial member 32 by tabs 44 received in slots 46.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dial member 32 and, as described later, cooperates with a clutch to selectively couple dial member 32 with a dose button. As shown, skirt 42 provides a surface external of body 11 to enable a user to rotate dose dial member 32 for setting a dose.

Skirt 42 illustratively includes a plurality of surface contours 48 and an annular ridge 49 formed on the outer surface of skirt 42. Surface contours 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose dial member 32 for dose setting.

Delivery device 10 includes an actuator 50 having a clutch 52 which is received within dose dial member 32. Clutch 52 includes an axially extending stem 54 at its proximal end. Actuator 50 further includes dose button 56 positioned proximally of skirt 42 of dose setting member 30. Dose button 56 includes a mounting collar 58 (FIG. 2) centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 there between. Face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" may equal one-half or one unit of medication. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 2), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10. Alternatively, the device may be configured such that in the course of dose setting, skirt 42 and dose button 56 move only rotationally relative to housing 12 (that is, without spiraling out), and dose dispensing is initiating after dose setting by applying axial force to the module coupled to dose button 56.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow back driving rotation of dose setting member 30 relative to actuator 50 and housing 12. Also, since dose setting member 30 and actuator 50 are free to relatively rotate, actuator 50 is held from rotating relative to device housing 12 by the user's engagement of dose button 56 by pressing against it.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The dose delivered may be derived based on the rotation of dose setting member 30 relative to actuator 50 during dose delivery. This rotation may be determined by detecting the incremental movements of the dose setting member which are "counted" as the dose setting member is rotated during dose delivery.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein.

The dose detection systems use a sensing component and a sensed component attached to members of the medication delivery device. The term "attached" encompasses any manner of securing the position of a component to another component or to a member of the medication delivery device such that they are operable as described herein. For example, a sensing component may be attached to a member of the medication delivery device by being directly positioned on, received within, integral with, or otherwise connected to, the member. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from an attachment where the components/members are coupled by one or more intermediate functional members, such as the way dose dial member 32 is coupled in FIG. 2 to dose button 56 by clutch 52.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor systems are contemplated herein. In general, the sensor systems comprise a sensing component and a sensed component. The term "sensing component" refers to any component which is able to detect the relative position or movement of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose detection system, the sensed component rotates relative to the sensing component, which is able to detect the rotational movement of the sensed component. The sensing component may comprise one or more sensing elements, and the sensed component may comprise one or more sensed elements.

The sensor system produces outputs representative of the movement of the sensed component. A controller is operably connected to the sensor to receive the outputs. The controller is configured to determine from the outputs the amount of dose delivered by operation of the medication delivery device.

Illustratively, the dose detection system includes an electronics assembly suitable for operation of the sensor system as described herein. A controller is operably connected to the sensor system to receive outputs from the rotation sensor. The controller is configured to determine from the outputs the amount of dose delivered by operation of the medication delivery device. The controller may include conventional components such as a processor, power supply, memory, microcontrollers, etc. Alternatively, at least some components may be provided separately, such as by means of a computer, smart phone or other device. Means are then provided to operably connect the external controller components with the sensor system at appropriate times, such as by a wired or wireless connection.

An exemplary electronics assembly 76 comprises a flexible printed circuit board (FPCB) having a plurality of electronic components. The electronics assembly comprises a sensor system including one or more sensors operatively communicating with a processor for receiving signals from the sensor representative of the sensed rotation. Electronics assembly 76 further includes a microcontroller unit (MCU) comprising at least one processing core and internal memory. The system includes a battery, illustratively a coin cell battery, for powering the components. The MCU includes control logic operative to perform the operations described herein, including determining a dose delivered by medication delivery device 10 based on a detected rotation of the dose setting member relative to the actuator. Many of the components of the electronics assembly may be contained in a compartment 78 located proximal of the dose button 56.

The MCU is operative to store the detected dose delivery in local memory (e.g., internal flash memory or on-board EEPROM). The MCU is further operative to wirelessly transmit a signal representative of the detected dose to a paired remote electronic device, such as a user's smartphone. Transmission may, for example, be over a Bluetooth low energy (BLE) or other suitable short or long range wireless communication protocol. Illustratively, the BLE control logic and MCU are integrated on the same circuit.

Disclosed herein is a medication delivery device including a dose detection system operable to determine the amount of dose delivered based on relative rotation between a dose setting member and the device body. The dose detection system utilizes a dose setting member attached to the device body and rotatable relative to the device body about an axis of rotation during dose delivery. A sensed element is attached to and rotationally fixed with the dose setting member. An actuator is attached to the device body and is held against rotation relative to the device body during dose delivery. The sensed element thereby rotates relative to the actuator during dose delivery in relation to the amount of dose delivered.

The dose detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable. The sensor system is operable to determine the total angular displacement of a dose setting member during dose delivery. Thus, if the angular displacement is 90°, then 5 units of dose have been delivered.

The angular displacement is determined by counting increments of dose amounts as the injection proceeds. For example, a sensing system may use a repeating pattern of a sensed element, such that each repetition is an indication of a predetermined degree of angular rotation. Conveniently, the pattern may be established such that each repetition corresponds to the minimum increment of dose that can be set with the medication delivery device.

The sensor system components may be permanently or removably attached to the medication delivery device. In an illustrative embodiment, as least some of the dose detection system components are provided in the form of a module that is removably attached to the medication delivery device. This has the advantage of making these sensor components available for use on more than one pen injector.

The sensor system detects during dose delivery the relative rotation of the sensed component, and therefore of the dose setting member, from which is determined the amount of a dose delivered by the medication delivery device. In an illustrative embodiment, a rotation sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery.

In one aspect, there is provided a dose detection system in the form of a module useful in combination with a medication delivery device. The module may carry various components of a sensor system, which therefore may be moved from one delivery device to another. The module in particular comprises a rotation sensor and other associated components such as a processor, memory, battery, etc. The module may be provided as a component which is removably attachable to the dose setting member, the actuator, or potentially other parts of the medication delivery device.

Illustratively, the dose detection module includes a body attached to dose button 56 and includes a cylindrical side wall and a top wall spanning over and sealing the side wall. By way of example, the module may include inwardly-extending tabs attaching the module to the annular lip 64 of dose button 56. In another approach, distal pressing of the module provides a sufficient frictional engagement between the module and dose button 56 as to functionally cause the module and dose button 56 to remain rotationally fixed together during dose delivery. However, attached, the module is rotationally fixed with the actuator so as not to rotate relative to the actuator during dose delivery. The module is provided such that pressing on the module delivers a set dose.

The dose detection system comprises a module including a rotation sensor attached to the actuator. The sensed element is rotationally fixed with the dose setting member and includes alternating, first and second surface features radially-spaced about the axis of rotation of the dose setting member. The rotation sensor includes a light source for emitting sensing light in a sensing direction during dose delivery. The rotation sensor further includes a light sensor positioned to receive the sensing light emitted in the sensing direction.

Rotation of the sensed element during dose delivery positions the first and second surface features in the path of the sensing light. The first surface features result in the sensing light being detected by the light sensor, the second surface features result in the sensing light not being detected by the light sensor. In one aspect, the first and second surface features may be uniformly configured and spaced intermittently around the axis of rotation of the sensed element. In a particular aspect, the surface features are equi-radially spaced about the axis of rotation.

In one embodiment, the first and second surface features comprise open and closed portions which operate to either allow the sensing light to pass through the open portions and ultimately to the light sensor, or to block the sensing light from passing through the closed portions to the light sensor. In this embodiment, the open and closed portions may be defined by apertures formed in a continuous surface, and in another aspect the open and closed portions may be defined by castellation's formed by alternating projections and recesses. In another embodiment, the first and second features may comprise surfaces which are reflective and non-reflective, respectively. The light emitted in the sensing direction is then either reflected or not reflected to the light sensor during rotation of the sensed element relative to the actuator during dose delivery.

The rotation sensor is responsive to the detection of the sensing light to detect rotation of the dose setting member relative to the actuator during dose delivery. The module may further comprise an electronics assembly including a controller responsive to the rotation sensor to determine the amount of dose delivery based on the detected rotation of the dose setting member relative to the actuator during dose delivery.

The sensing direction may be any that is detectable by the light sensor. For example, the sensing direction may be in a radial direction, orthogonal to the axis of rotation of the sensed element. Thus, the open portions may be provided as apertures in a cylindrical wall. Alternatively, the open portions may be formed by castellation's formed by axially directed projections extending proximally or distally from a support surface. As another example, the sensing direction may be in an axial direction, parallel to the axis of rotation of the sensed element. Thus, the open portions may be provided as apertures in a circular or annular wall. Alternatively, the open portions may be formed by castellation's formed by spaced, radially-directed projections extending inwardly or outwardly.

The sensed element is attached to or may be formed integrally with the dose setting member. Depending on the medication delivery device, the sensed element may be attached to the skirt, the flange or the dose dial, or any other component that rotates relative to the actuator and the device body during dose delivery in relation to the amount of dose delivered.

Figure 5:
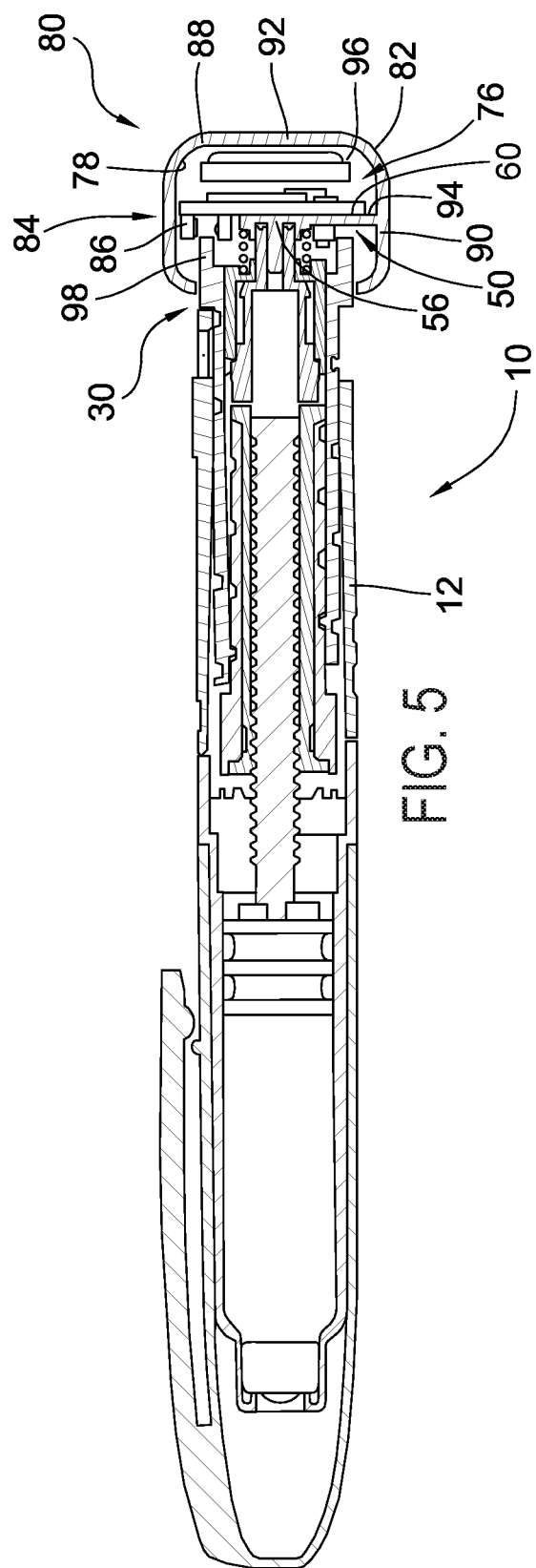
FIG. 5 is a side, diagrammatic view, partially in cross section, of an exemplary embodiment of a dose detection system shown attached to the proximal portion of a medication delivery device.

Referring to FIG. 5, there is shown in diagrammatic form a dose delivery detection system 80 including a module 82 useful in combination with a medication delivery device, such as device 10. Module 82 carries a sensor system, shown generally at 84, including a rotation sensor 86 and other associated components such as a processor, memory, battery, etc. Module 82 is optionally provided as a separate component which may be removably attached to actuator 50.

Dose detection module 82 includes a body 88 attached to dose button 56. Body 88 illustratively includes a cylindrical side wall 90 and a top wall 92, spanning over and sealing side wall 90. Body 88 further includes an attachment, such as shown at 94, attaching module 82 to dose button 56 such that pressing on the module delivers a set dose. Dose detection module 82 may be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein.

During dose delivery, dose setting member 30 is free to rotate relative to dose button 56 and module 82. In the illustrative embodiment, module 82 is rotationally fixed with dose button 56 and does not rotate during dose delivery. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from proximal face 60 of dose button 56 and thereby provides a compartment 78 containing some or all of electronics assembly 76. Compartment 78 defines a chamber 96 and may be open at the bottom, or may be enclosed, such as by a bottom wall.

Figure 6:
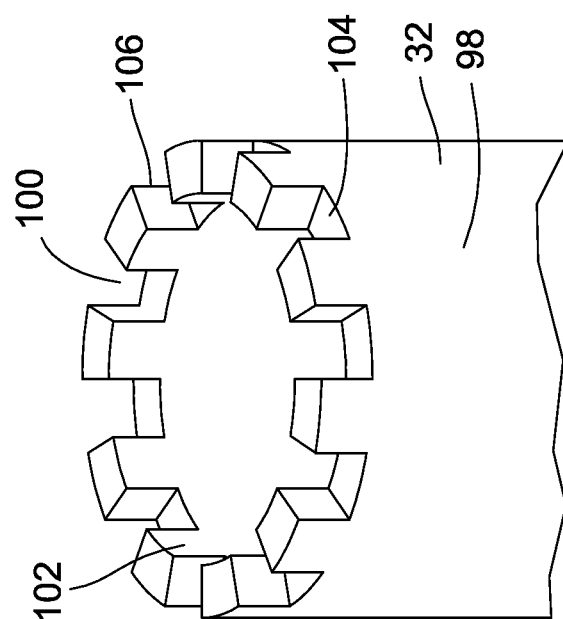
FIG. 6 is a perspective view of a sensed element of the sensor system of FIG. 5.

In FIG. 6 there is shown an example of a sensed element 98 including alternating open portions 100 and closed portions 102. In the embodiment of FIG. 6, the open and closed portions are formed by castellation's, in which the open portions are formed by recesses 104 between spaced projections 106. Projections 106 extend axially in the proximal direction. It will be appreciated, however, that the open portions may instead comprise apertures in an otherwise solid wall. The open and closed portions are shown as being formed in a proximal extension of dose dial 32, but it will be appreciated that they may also be formed in other dose setting members, such as flange 38 or skirt 42.

Figure 7:
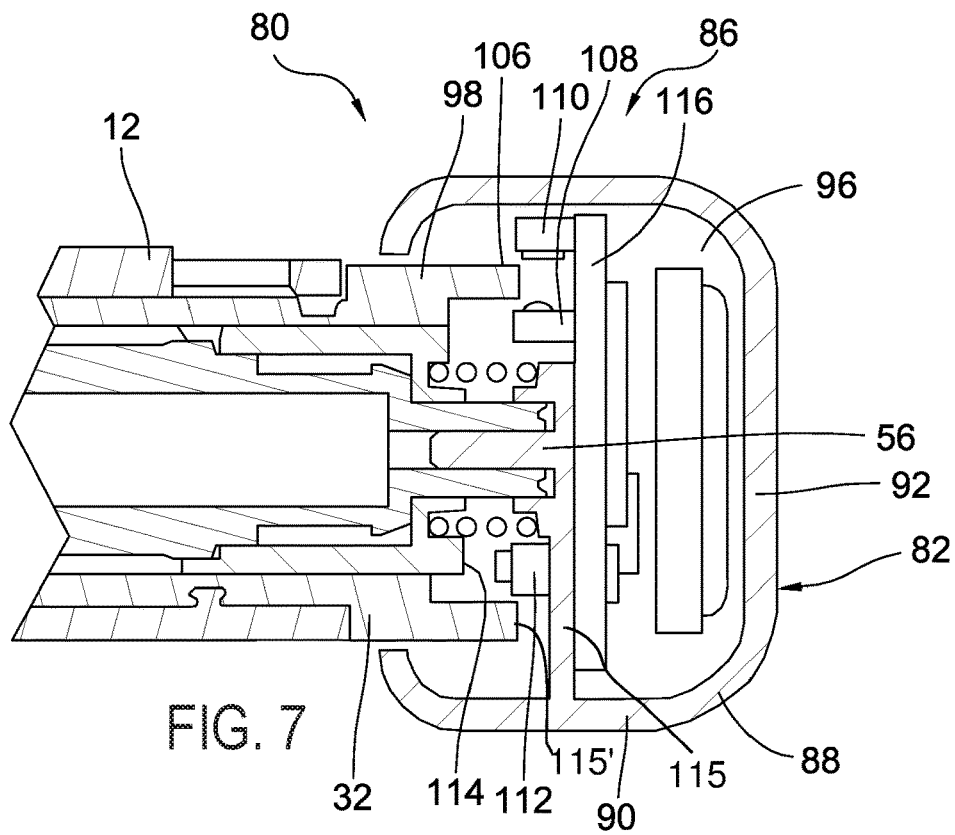
FIG. 7 is a side, diagrammatic view, partially in cross section, of the dose detection system of FIG. 5 in the dose setting mode.
Figure 8:
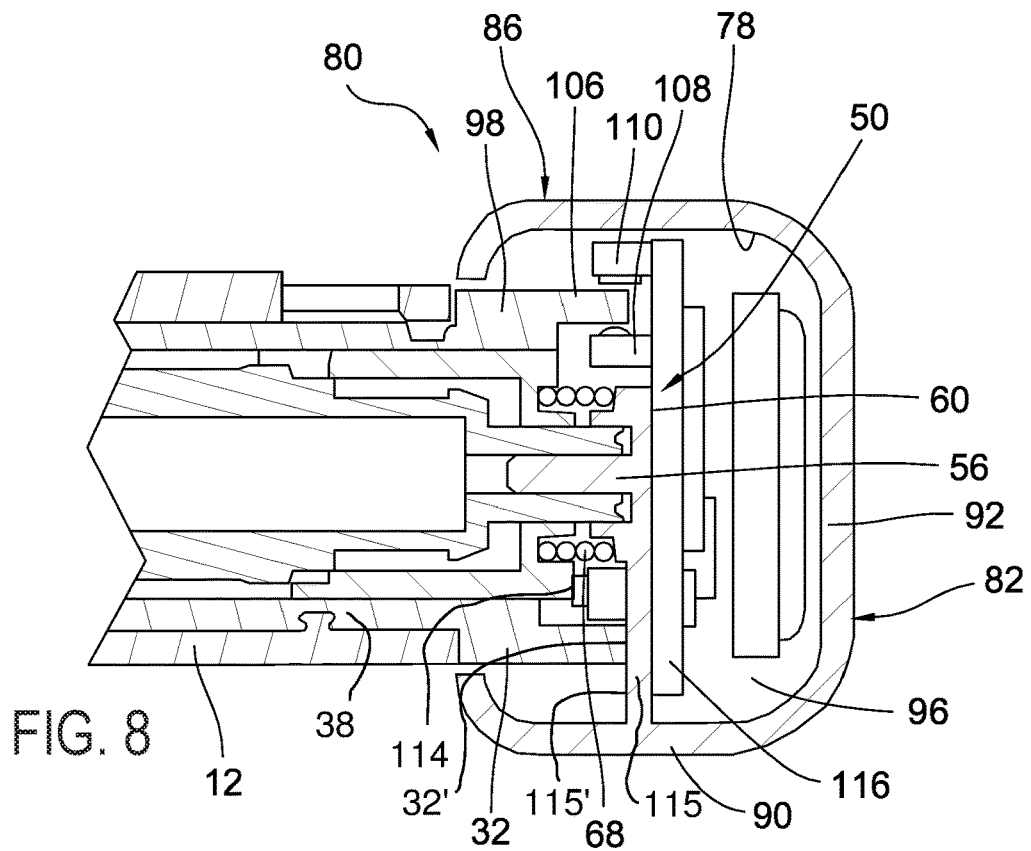
FIG. 8 shows the dose detection system of FIG. 7 with the module pressed distally as in the dose delivery mode.

Referring to FIGS. 7 and 8, there are shown two different positions for module body 88 relative to device housing 12. In FIG. 7, the module is in a first operating mode in which the module may be used to set a dose. In certain embodiments, the module and dose button are rotationally fixed to the dose setting member in this mode, and module body 88 may be rotated to set a dose. In this position, projections 106 are axially displaced from the light source 108 and the light sensor 110. In addition, wake-up switch 112 is displaced from contact 114 defined by the axial proximal end of flange 38. Triggering of wake-up switch 112 is configured to allow power transmission from the power source (or battery) for powering up the electronic components for dose sensing in order to minimize inadvertent power loss or usage when a dose dispensing event is not occurring. As shown, wake-up switch 112 may be located along the bottom side or distally facing end 115' of an intermediate body wall 115 of module 82 that at least partially transverses an intermediate portion of chamber 96 cavity defined by body 88 of module 82. As shown, contact 114 may be located radially inward from housing of dose dial 32 and in a more distal location relative to an axial proximal end 32' of the wall of dose dial 32. Wake-up switch 112 is shown disposed radially between external part of spring 68 and the interior luminal surface of dose dial 32. Due to the tight area in which the components are packaged, it may be beneficial to position wake-up switch 112 circumferentially offset from light source 108 and sensor 110, such as for example, about 180 degrees from one another.

Upon pressing top wall 92 of module 82, dose button 56 advances distally relative to housing 12, compressing spring 68. Wake-up switch 112 is triggered by being pressed against contact 114, and the electronics assembly is activated. In order to prevent over depression of the button that could lead to component damage, the axial extent of travel of dose button/module combination may be limited. For example, axial proximal end 32' of the wall of dose dial 32 may define a physical stop that in is in a contacting relationship with distally facing end 115' of intermediate body wall 115 of module 82. Such physical stop may also aid in alignment of said sensing components for more accurate and consistent readings. At the same time, rotation sensor 86 is advanced such that projections 106 are received between light source 108 and light sensor 110 (FIG. 8). Continued pressing of the module distally results in back driving dose dial 32 in a spiral direction relative to housing 12. FIG. 8 shows the medication delivery device with module 82, and therefore dose button 56, still depressed but with dose dial 32 having been driven back to the zero dose position relative to housing 12.

In the embodiment of FIGS. 5-8, light source 108 and light sensor 110 are shown attached to a printed circuit board ("PCB") 116 attached to actuator 50. In this configuration, light source 108 is positioned to emit sensing light in a radially-outward sensing direction. Light sensor 110 is positioned in alignment with light source 108 to directly receive the sensing light. As sensed element 98 rotates, recesses 104 and projections 106 will successively be positioned in line with the sensing light being emitted in the sensing direction.

Figure 9:
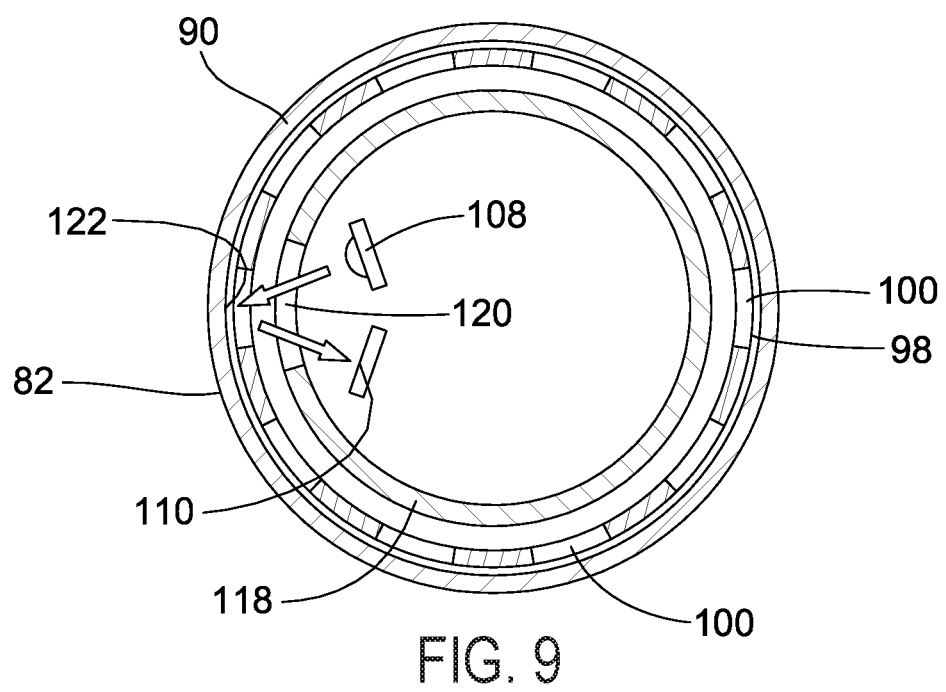
FIG. 9 shows an alternate dose detection system involving the use of reflected light.

In an alternate embodiment, light sensor 110 is positioned to receive reflected light rather than direct light. Referring to FIG. 9, there is shown diagrammatically a dose detection system similarly using alternating open and closed portions of the dose setting member. This embodiment is comparable to the embodiment of FIGS. 5-8, except for the positioning of the light source and light sensor. In FIG. 9, light source 108 and light sensor 110 are positioned interior of a cylindrical wall 118 including an opening 120. Side wall 90 of module 82 includes a reflective surface 122 aligned with opening 120. Light source 108 is directed outwardly at a slight angle from radially to emit sensing light through opening 120 in wall 118. Light emitted in this direction and passing through open portions 100 in sensed element 98 is reflected back through opening 120 and is received by light sensor 110.

In either approach, light receptor 110 operates to detect when the sensing light is and is not received by light sensor 110 and rotation sensor 86 is thereby able to detect rotation of dose setting member 30 relative to actuator 50 during dose delivery.

Figure 10:
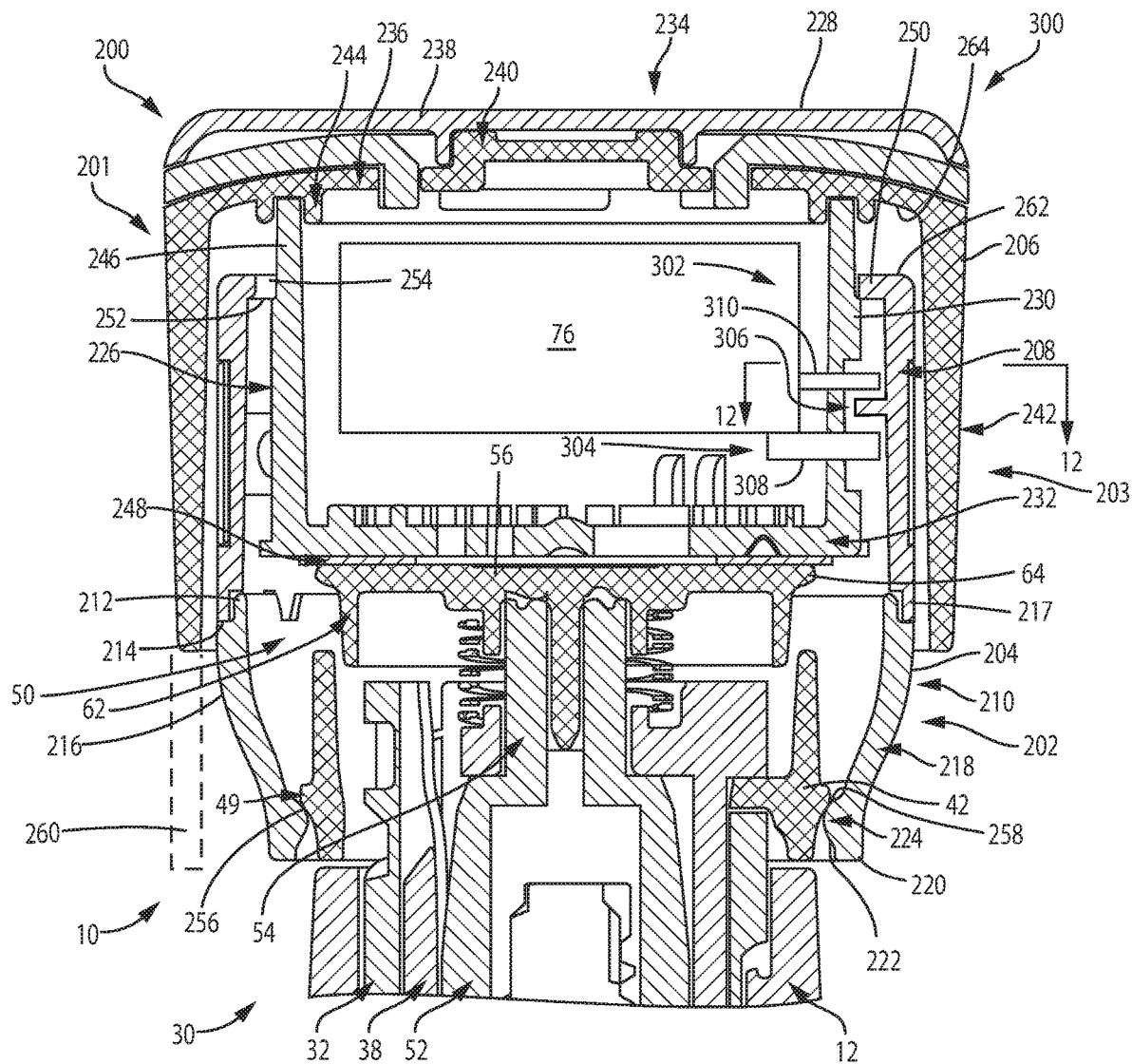
FIG. 10 is a cross-sectional view showing another illustrative embodiment of the dose detecting module installed on a medication delivery device.

Referring to FIG. 10, medication delivery device 10 includes a module 200 having a housing assembly 201 comprising a coupling component 202 and a dosing component 203. Coupling component 202 includes a first housing portion 204. Dosing component 203 includes a second housing portion 206 coupled to first housing portion 204. As described herein, first and second housing portions 204, 206 are rotatable relative to each other about a longitudinal axis and are axially moveable relative to each other along the axis. First housing portion 204 includes a coupling wall 208, illustratively in the form of a cylinder, and a coupling member 210 fixed to a distal end of coupling wall 208. Coupling wall 208 and coupling member 210 may be fixed together via any suitable fastening means, such as a weld, snap fit, threaded interface, etc., or alternatively may be integrally formed as a single component. In an illustrative embodiment, coupling member 210 includes an annular ridge 212 that extends axially from the proximal end forming an annular shoulder 214 between ridge 212 and an outer surface 216 of coupling member 210. The distal end of coupling wall 208 includes projection 217 which snap fits onto coupling member 210 to rotationally and axially fix coupling member 210 to coupling wall 208. When coupled together, the distal end of coupling wall 208 abuts annular shoulder 214 of coupling member 210.

Coupling member 210 includes an annular ring portion 218 sized to receive skirt 42 and to engage the outer surface of skirt 42 for attaching first housing portion 204 to delivery device 10. As illustrated, outer surface 216 of coupling member 210 tapers radially inwardly from shoulder 214 to ring portion 220 such that a proximal end diameter of coupling member 210 is larger than a distal end diameter of coupling member 210. An inner surface 222 of ring portion 220 includes a plurality of contour features 224, illustratively variably sized projections and grooves, that are sized to engage corresponding surface contours 48 (e.g., grooves) of skirt 42 for coupling thereto. In the illustrated embodiment, surface contours 48 of coupling member 210 couple to annular ridge 49 of skirt 42 via a snap fit or an interference fit, although any other suitable fastening mechanism may alternatively be used to couple first housing portion 204 to skirt 42.

In the illustrative embodiment, contour features 224 and surface contours 48 are sized, shaped, and spaced to provide mechanical keying of housing assembly 201 to delivery device 10. In particular, in the illustrative embodiment, housing assembly 201 is mechanically keyed via contour features 224 to be compatible with a specific type or types of delivery devices having compatible surface contours 48, such as based on medication type, concentration, strength, volume, and/or formulation, as well as cartridge size or other aspects of the corresponding delivery device. In some embodiments, electronics assembly 76 of module 200 is pre-programmed to operate based on the compatible delivery device(s) and/or medication. Such mechanical keying serves to reduce the likelihood that detection module 200 is used with an incorrect delivery device and/or medication.

With the mechanical key feature, module 200 must be in proper rotational alignment with skirt 42 of device 10 to slide and snap coupling member 210 onto skirt 42. Coupling member 210 illustratively may be provided with a projection or other visual reference on its outer surface 216 that serves as a guide for rotationally aligning module 200 to skirt 42. Other keying features, such as color coding, may be used to identify a correct module 200 for a corresponding medication delivery device 10.

Second housing portion 206 includes a drum 226 and a cap portion 228 coupled to a proximal end of drum 226. Drum 226 illustratively includes inner wall 230 and a disc-shaped base wall 232 at a distal end of inner wall 230. Cap portion 228 includes an end wall 234 positioned orthogonally to inner wall 230. End wall 234 illustratively includes a distal wall portion 236 and a proximal wall portion 238 coupled to distal wall portion 236 at a centrally located mounting interface 240 via a snap fit, interference fit, ultrasonic weld, or other suitable coupling mechanism. Cap portion 228 further includes an outer wall 242 radially spaced apart from and substantially parallel to inner wall 230. In the illustrated embodiment, coupling wall 208 of first housing portion 204 is positioned in the gap formed radially between outer wall 242 and inner wall 230 of second housing portion 206. End wall 234 of cap portion 228 includes a mounting collar 244 axially extending from and centrally located on distal wall portion 236. Upper wall portion 246 of inner wall 230 is fixed to mounting collar 244 via any suitable coupling mechanism, such as ultrasonic weld or interference fit for example.

When module 200 is attached to delivery device 10, a distal surface of base wall 232 abuts the proximal end surface of dose button 56. Illustratively, the distal surface of base wall 232 includes a thin, disc-shaped friction pad 248 having a central opening. Pad 248 provides frictional resistance (e.g., via surface roughness and/or adhesive) between base wall 232 and dose button 56 such that second housing portion 206 remains rotationally coupled to dose button 56 during a dosing operation of module 200 with device 10. Base wall 232 of drum 226 in some embodiments may include a centrally located, axially extending projection (not shown) configured for receipt within a recessed portion of dose button 56, such as for coupling and/or alignment of dose button 56 and base wall 232.

In the illustrated embodiment, when dose detection module 200 is attached to delivery device 10, first and second housing portions 204, 206 and skirt 42 are coaxial and are thus operative to rotate together about a same longitudinal axis during a dose setting operation of delivery device 10. In addition, first and second housing portions 204, 206 are operative to move axially together with skirt 42 along the longitudinal axis during the dose setting operation and axially relative to each other along the longitudinal axis in response to an axial force on second housing portion 206 to start the dose delivery operation. While coupling wall 208 and inner wall 230 of respective first and second housing portions 204, 206 illustratively extend 360 degrees about the longitudinal axis of module 200, walls 208, 230 alternatively may extend a portion of the full circumference about the axis. In other words, circumferential walls 208, 230 may include one or more breaks in the respective wall somewhere along the perimeter rather than being continuous walls as illustrated.

Dose detection module 200 is configured for operation in at least a first operating mode and a second operating mode. In the illustrated embodiment, the first operating mode corresponds to the dose setting operation of delivery device 10, and the second operating mode corresponds to the dose dispensing operation of delivery device 10. In the first operating mode, shown in FIG. 10, first and second housing portions 204, 206 are at a home position axially wherein second housing portion 206 is not axially compressed relative to first housing portion 204. In this first operating mode, first and second housing portions 204, 206 are rotationally locked together by a locking mechanism, illustratively a tooth and slot coupling.

The proximal end of coupling wall 208 of first housing portion 204 includes a radially extending annular lip 250 having a plurality of circumferentially spaced slots 252 formed therein. Slots 252 are each sized to receive a tooth or tongue 254 formed on the outer surface of upper wall portion 246 of inner wall 230. Illustratively, four teeth are spaced 90 degrees apart around upper wall portion 246, and twenty slots 252 are equally spaced around lip 250, although any suitable number of teeth and slots may be provided. In the illustrative embodiment, the number of slots 252 is the same as the number of rotational increments or clicks to which dose setting member 30 of device 10 may be set in one complete rotation of dose dial member 32 relative to housing 12. The multiple slots allow first housing portion 204 and second housing portion 206 to lock together in the first operating mode in multiple relative rotational positions, with more slots providing more possible relative positions. In an alternative embodiment, slots 252 may be formed on inner wall 230 and teeth formed on coupling wall 208. Other suitable rotational locking mechanisms may be provided.

In general, dosing component 202 in the first operating mode during dose setting is axially and rotationally fixed to coupling component 202. In this first mode, dosing component 203 may be grasped by the user and rotated relative to device body 11. Due to the connections between dosing component 203 and coupling component 202, and between coupling component 202 and dose setting member 30, the rotation of dosing component 203 results in rotation of dose setting member 30 and a dose is set. During dose setting, actuator 50, including dose button 56, is connected by way of clutch 44 to dose setting member 30 and spirals with dose setting member 30 relative to device body 11.

In one embodiment, dosing component 203 includes inner wall 230 and outer wall 242, and coupling component 202 includes coupling wall 208 received between the inner and outer walls. Dose setting member 30 includes an exposed circumferential surface 256, optionally including surface contours 48, for use in rotating dose setting member 30 relative to device body 11. Coupling wall 208 extends distally beyond inner wall 230 and includes a coupling portion 258 attached to exposed circumferential surface 256 of dose setting member 30 in order to attach coupling component 202 to dose setting member 30. In another aspect, as shown at 260, outer wall 242 extends distally to radially overlap some or all of the exposed circumferential surface 256 of the dose setting member and/or the coupling member 210.

Dosing component 203 is rotationally locked with coupling component 202 during dose setting. As previously indicated, this may be accomplished by way of a variety of locking mechanisms. Illustratively, coupling wall 208 is received in the gap between inner wall 230 and outer wall 242. As described, the locking mechanism may comprise mechanical features, such as teeth received within slots, or complementary shaped, mutually-facing teeth extending axially from the coupling and dosing components. The teeth in either event may, for example, be formed on coupling wall 208 of coupling component 202 and on one of the inner and outer walls 230, 242 of dosing component 203. In a further aspect, to reduce the risk of damage to the medication delivery device, the locking mechanism is configured to cause disengagement of the dosing component from the coupling component in the event that a rotational force is applied from the dosing component to the coupling component in excess of a predetermined amount.

Illustratively, the locking mechanism is configured also to allow for disengagement upon axial movement of dosing component 203 toward coupling component 202. Once disengaged, coupling component 202 is free to rotate relative to dosing component 203. Axial movement of actuator 50 in the direction of dose setting member 30 results in clutch 52 disconnecting the rotational engagement of actuator 50 with dose setting member 30. In one aspect, pressing housing assembly 201 moves dosing component 203 closer to coupling component 202 and coupling component 202 is thereby rotationally disengaged from dosing component 203. This occurs before actuator 50 moves a sufficient distance to initiate dose delivery. In another aspect, a wake-up switch, such as described above, is provided to cause relevant components of electronics assembly 76 to activate in time to detect the dose delivery. In another aspect, pressing housing assembly 201 disengages dosing component 203 from coupling component 202 and engages the wake-up switch, and subsequent distal movement presses dose button 56 sufficiently to cause dose delivery. Although not shown, such wake-up switch may be positioned within cavity defined by wall portion 62 of dose button 56 and configured to contact the dose dial 32 or flange 38 when in the second mode. In other embodiments, the wake-up switch may be other configurations, such as electrical contacts or accelerometer and may be positioned within the module body.

Although not required, the disengagement of dosing component 203 from coupling component 202 may occur such that there is no contact between those two components once disengaged. For example, the upper end 262 of coupling wall 208 may be spaced apart from mounting collar 244 and the interior 264 of distal wall portion 236. Providing such a space avoids contact between coupling wall 208 and outer wall 242, which could otherwise provide frictional resistance to rotation of coupling component 202 relative to dosing component 203 during dose delivery.

In the second operating mode of module 200, the locking mechanism is disengaged, and first and second housing portions 204, 206 are rotatable relative to each other. An axial movement or compression of second housing portion 206 relative to first housing portion 204 is operative to transition module 200 from the first operating mode to the second operating mode by disengaging the locking mechanism to allow relative rotation of first and second housing portions 204, 206 about the longitudinal axis of module 200. In particular, the axial movement of second housing portion 206 towards first housing portion 204 causes teeth 254 to axially slide out of corresponding slots 252 to rotationally uncouple first and second housing portions 204, 206.

In general, in the second operating mode during dose delivery, coupling component 202 is rotatable relative to dosing component 203. In this second mode, dosing component 203 is axially and rotationally fixed to actuator 50. Dosing component 203 is axially fixed in that the dosing component bears against actuator 50 as housing assembly 201 is pressed distally to deliver a dose. Further, dosing component 203 is rotationally fixed to actuator 50 either by a frictional engagement or by other locking means as previously described. During dose delivery, actuator 50, including dose button 56, is pressed by the user and translates axially, while being held from rotating relative to device body 11. Since clutch 52 has released the rotational connection between actuator 50 and dose setting member 30, the dose setting member spirals back into device body 11.

In the first operating mode with module 200 coupled to delivery device 10, a rotational or screw force on module 200, such as applied to outer wall 242 or any other user accessible portion, causes corresponding rotation and axial motion of dose setting member 30 to operate medication delivery device 10 in the dose setting mode described herein. In the second operating mode with module 200 coupled to delivery device 10, the axial force which compresses module 200 is transferred to dose button 56 and thereby rotationally disengages actuator 50 from dose setting member 30, causing dose setting member 30 to screw back into housing 12 to operate device 10 in the dose delivery mode. During the dose delivery operation of device 10, first housing portion 204 screws (moves axially and rotationally) with dose setting member 30 while second housing portion 206 remains rotationally fixed while moving only axially with dose setting member 30. In an exemplary mode of use for attachment of module 200 to device 10, the user aligns the visual alignment feature(s) of module 200 and device 10, and module 200 is snap fitted to dose setting member 30 of device 10. The locking mechanism (e.g., teeth 254 and slots 256) ensures proper alignment of the rotational sensor.

In an exemplary mode of use for dialing a dose, dosing component 203 of module 200 is rotated relative to housing 12 of device 10, and such rotation is translated to dose setting member 30 to screw dose dial member 32 up to the desired dose amount. In an exemplary mode of use for injecting a dose, cap portion 228 of module 200 is axially pushed relative to housing 12 to start an injection. The axial force disengages the locking mechanism in module 200 and the clutch 52 in delivery device 10, and first housing portion 204 is free to rotate relative to second housing portion 206 and dose dial member 32 is free to rotate relative to dose button 56 of device 10.

When injection ends, the user releases cap portion 228, and electronic assembly 76 captures the injection event until a certain timeout period, stores the dose information, and starts activity in order to automatically update the app running in the remote smartphone. In case of a transmission failure, manual sync of module 200 with the smartphone is possible later to transmit the dose information. Following transmission, module 20 transitions again to deep sleep state (low power mode). In an exemplary mode of use for detaching module 200 from device 10, module 200 is detached by pulling module 200 with the required force away from device 10.

Further details of the design and operation of an exemplary medication delivery device may be found in U.S. Pat. No. 7,291,132, entitled Medication Dispensing Apparatus with Triple Screw Threads for Mechanical Advantage, the entire disclosure of which is hereby incorporated by reference herein.

Figure 11:
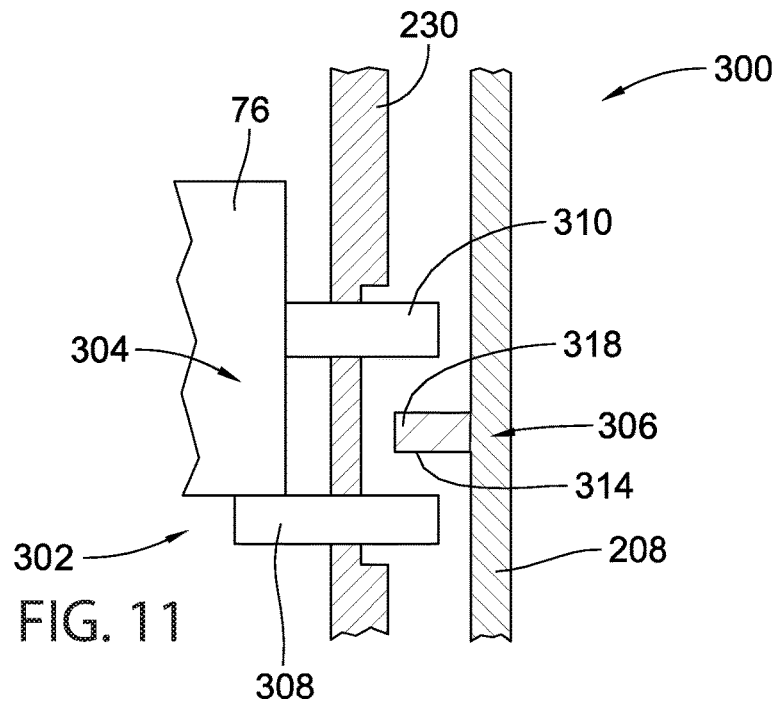
FIG. 11 is a partial, cross-sectional view showing a sensor and sensed element of another illustrative embodiment of the dose detection system.
Figures 12, 13:
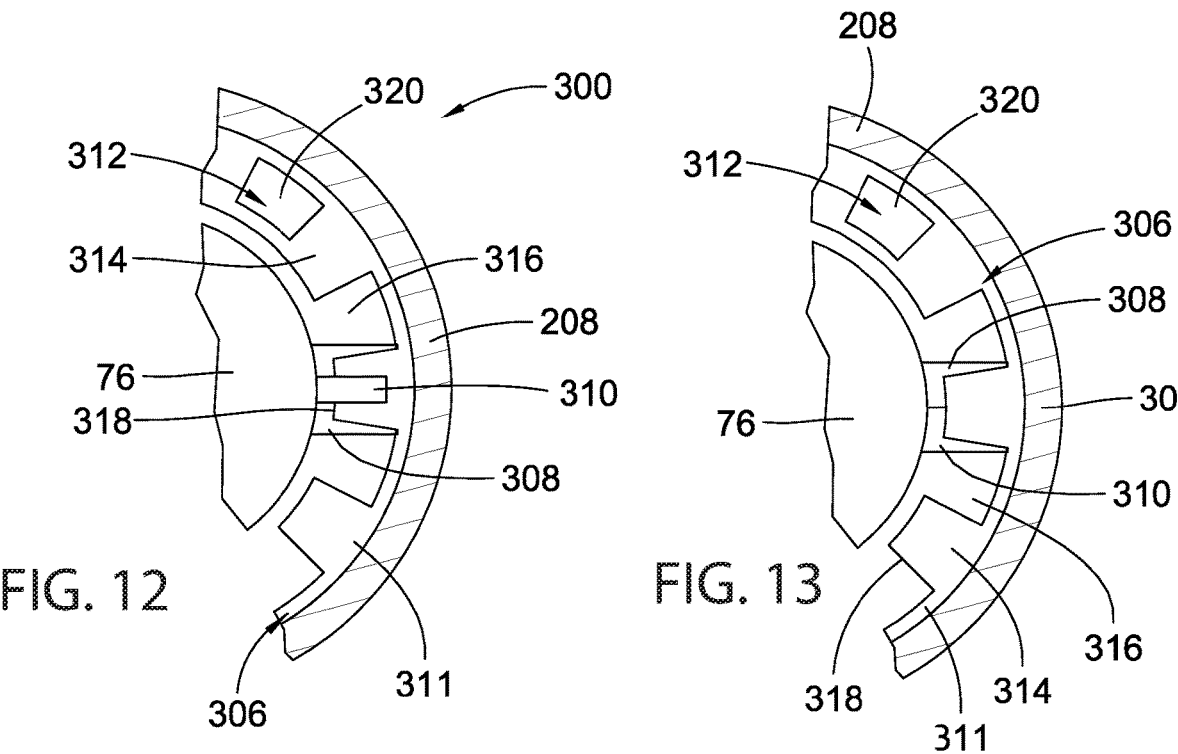
FIG. 12 is a partial, cross-sectional view of the dose detection system of FIG. 11 taken along line 12-12, and showing detection based on axially transmitted light.
FIG. 13 is a partial cross-sectional view of an alternate embodiment to that of FIG. 12 detecting reflected light.

In reference to FIGS. 10-12, an alternate embodiment for the dose detection system is shown in combination with a medication delivery device 10. Dose detection system 300 includes housing assembly 201 including coupling component 202 and dosing component 203. Module 200 carries a sensor system, shown generally at 302, including a rotation sensor 304 and a sensed element 306. As before, module 200 may be provided as a separate component which may be removably attached to the actuator, or the components of module 200 may be integrated into the medication delivery device.

Rotation sensor 304 is shown attached to inner wall 230 and comprises two components, a light source 308 and a light sensor 310. Both light source 308 and light sensor 310 are operatively connected to electronic assembly 76. For example, light source 308 and light sensor 310 may be attached to a printed circuit board ("PCB") forming a part of electronics assembly 76. Rotation sensor 304 operates in conjunction with sensed element 306 which is shown attached through coupling wall 208 and coupling member 210 to dose setting member 30, for example skirt 42. Illustratively, sensed element 306 is attached to or is integral with coupling wall 208. Although shown as separate elements, coupling member 210 may be formed integral with coupling wall 208.

Sensed element 306 in general has an annular shape 311 and is attached to the interior of coupling wall 208. Sensed element 306 includes alternating open portions 312 and closed portions 314. In the embodiment of FIG. 12, the open and closed portions are formed by castellation's, in which the open portions are formed by recesses 316 between spaced projections 318. Projections 318 extend radially-inward. It will be appreciated that the open portions 312 may instead comprise apertures 320 in an otherwise solid sensed element 306. Alternatively, sensed element 306 may be formed integral with coupling wall 208. For example, sensed element 306 may be formed as spaced projections attached to or integral with coupling wall 208 and extending radially inward. The open and closed portions are shown as being attached through coupling wall 208 and coupling member 210 to skirt 42. However, coupling wall 208 may also be attached to any other component of dose setting member 30, including for example dose dial 32 or flange 38.

Referring to FIGS. 11-12, further details of dose detection system 300 are shown. Light source 308 and light sensor 310 are positioned in FIG. 11 such that light is emitted by light source 308 in an axial, distal direction. As shown, the light source 308 and light sensor 310 radially overlap with projection 318. In this design, the spacing of projections 318 may be such as to allow assembly of the module, for example by passage of light source 308 and/or light sensor 310 between projections 318. This may be further facilitated by a keyed connection providing alignment of first housing portion 204 with second housing portion 206. The embodiment of FIG. 11 may alternatively be configured such that radially overlapping does not exist in the assembled module.

Rotation of sensed element 306 relative to rotation sensor 304 occurs during dose delivery. The open and closed portions of sensed element 306 are positioned to intermittently prevent light from light source 308 being received by light sensor 310. These intermittent conditions are detected and used to determine rotation of dose setting member 30 relative to actuator 50 during dose delivery, and the amount of dose delivered is derived therefrom.

Dosing component 203 is shown in FIG. 10 in the at-rest position with a dose not having been set, as shown by the fact that dose dial 32 and skirt 42 are adjacent device housing 12. In setting a dose, the entire housing assembly 201 will translate and rotate away from device housing 12. In order to deliver the dose, dosing component 203 is pressed in the direction of coupling component 202 and is axially displaced closer to coupling component 202. To accommodate this relative axial movement, light source 308 and light sensor 310 are axially spaced sufficiently to allow the axial movement of sensed element 306.

In the method of using dose detection system 300, the dose is set by use of module 200, and particularly outer wall 242. Dose delivery is initiated by pressing module 200 distally and causing back driving of dose setting member 30 in a spiral direction relative to housing 12. Light source 308 is positioned to emit sensing light in an axial sensing direction. Light sensor 310 is positioned in alignment with light source 308 to directly receive the sensing light. As sensed element 306 rotates, recesses 316 and projections 318 will successively be positioned in line with the sensing light being emitted in the sensing direction.

In an alternate embodiment, light sensor 310 is positioned to receive reflected light rather than direct light. Referring to FIG. 13, there is shown diagrammatically a dose detection system similarly using alternating open and closed portions of the dose setting member 30. This embodiment is comparable to the embodiment of FIG. 12, except for the positioning of light source 308 and light sensor 310. Light source 308 emits light at a slight angle to axial. As a projection 318 passes in front of the light, the sensing light is reflected back off of the projection and impinges on the light sensor 310.

There have thus been described illustrative embodiments of a medication delivery device including a module providing components useful to detect the amount of a delivered dose. The medication delivery device includes a device body and a dose setting member attached to the device body and rotatable relative to the device body about an axis of rotation during dose delivery. The device also includes a sensed element attached to and rotationally fixed with the dose setting member, the sensed element including alternating first and second surface features radially-spaced about the axis of rotation of the dose setting member. An actuator is attached to the device body and is non-rotatable relative to the device body during dose delivery, and the sensed element rotates relative to the actuator during dose delivery in relation to the amount of dose delivered.

A module is axially and rotationally fixed with the actuator during dose delivery. The module comprises a rotation sensor including a light source emitting sensing light in a sensing direction during dose delivery. The rotation sensor further includes a light sensor positioned to receive the sensing light emitted in the sensing direction. Rotation of the sensed element during dose delivery positions the first and second surface features in the path of the sensing light. The first surface features result in the sensing light being detected by the light sensor, and the second surface features result in the sensing light not being detected by the light sensor. The rotation sensor is responsive to the detection of the sensing light to detect rotation of the dose setting member relative to the actuator during dose delivery. The module further comprises an electronics assembly responsive to the rotation sensor to determine the amount of dose delivery based on the detected rotation of the dose setting member relative to the actuator during dose delivery.

Illustratively in one embodiment, the module has a first operating mode and a second operating mode relative to said actuator. The module in the first operating mode during dose setting is directly attached to the actuator and is axially and rotationally fixed to the dose setting member. The module in the second operating mode is axially and rotationally fixed to the actuator and is rotatable relative to the dose setting member during dose delivery. The module optionally moves axially distally from the first operating mode to the second operating mode.

In an alternate embodiment, the dose detection system includes a coupling component which is attached directly to the dose setting member. The dose detection system further includes a dosing component which is axially and rotationally fixed to the actuator in a second operating mode during dose delivery. The coupling component and the dose setting member are rotatable relative to the actuator and the dosing component during dose delivery. In one aspect, the dosing component moves axially distally from the first operating mode to the second operating mode. In another aspect, the coupling component is axially fixed to the dosing component during dose setting, and is rotatable relative to the dosing component during dose delivery. In an exemplary form, the dose setting member includes an exposed circumferential surface for use in rotating the dose setting member relative to the device body for setting a dose, and the coupling component includes a coupling portion attached to the exposed circumferential surface of the dose setting member.

In one aspect, the dose detection system is originally incorporated into a medication delivery device as an integrated system. In another aspect, there is disclosed a modular form of the dose detection system. The use of a removably attached module is particularly adapted to use with a medication delivery device in which the actuator and/or the dose setting member include portions external to the device housing. These external portions allow for direct attachment of the module to the actuator, such as the dose button or skirt, and also attachment of the sensed element to the dose setting member, such as a skirt, flange, or dose dial member. Alternatively, the sensed element is integral with the medication delivery device and the module is removably attached. This has the advantage that the more complex and expensive electronics, including the rotation sensor and controller, may be reused with different medication deliver devices. By comparison, the sensed element may use relatively simple features, for example radially-spaced projections, which do not add significantly to the cost of the medication delivery device. Any of the devices described herein may comprise any one or more of medications described herein, such as, for example, within the cartridge of the device.

The invention claimed is:

1. A medication delivery device comprising:
a device body;
a dose setting member attached to said device body and rotatable relative to said device body about an axis of rotation during dose delivery;
a sensed element rotationally fixed with said dose setting member, said sensed element including alternating first and second surface features radially-spaced about the axis of rotation of said dose setting member, in which the surface features comprise alternating projections and recesses, said sensed element and said dose setting member rotating relative to said device body during dose delivery in relation to an amount of dose delivered;
a rotation sensor including a light source emitting sensing light in an axial direction during dose delivery, and a light sensor positioned to receive the sensing light during dose delivery, wherein the light source and the light sensor are axially disposed relative to one another, wherein in response to rotation of said sensed element during dose delivery the alternating first and second surface features are positioned directly between the light source and the light sensor in a path of the sensing light to vary light intensities detected by the light sensor; and
an electronics assembly responsive to the rotation sensor to determine the amount of rotation of the sensed element based on detection of the varying light intensities.

2. The medication delivery device of claim 1 in which the surface features comprise reflective and non-reflective surfaces.

3. The medication delivery device of claim 1 in which the surface features comprise alternating open and closed portions of said sensed element.

4. The medication delivery device of claim 1 in which the projections extend radially.

5. The medication delivery device of claim 4 in which said dose setting member is a skirt.

6. The medication delivery device of claim 5 in which the light sensor is positioned to directly receive light emitted by the light source.

7. The medication delivery device of claim 1 in which said dose setting member is a dose dial.

8. The medication delivery device of claim 1 comprising a reservoir disposed within the device body, the reservoir including a medication.

9. A medication delivery device comprising:
a device body;
a dose setting member attached to said device body and rotatable relative to said device body about an axis of rotation during dose delivery;
a sensed element rotationally fixed with said dose setting member, said sensed element including alternating first and second surface features radially-spaced about the axis of rotation of said dose setting member, the alternating first and second surface features extending radially relative to the axis of rotation, said sensed element and said dose setting member rotating relative to said dose body during dose delivery in relation to an amount of dose delivered, in which the sensed element has an annular shape, in which the alternating first and second surface features comprise alternating closed and open portions defined by the sensed element;
a rotation sensor including a light source emitting sensing light in a sensing direction during dose delivery, and a light sensor positioned to receive the sensing light emitted in the sensing direction during dose delivery, wherein in response to rotation of said sensed element during dose delivery the alternating first and second surface features are positioned in a path of the sensing light to vary light intensities detected by the light sensor, wherein one of the light source and the light sensor is disposed proximal to the other of the light source and the light sensor, and the alternating first and second surface features are disposed axially between the light source and the light sensor in a radially overlapping arrangement, in which the light sensor and the light source are attached to a housing portion disposed radially relative to the sensed element; and
an electronics assembly responsive to the rotation sensor to determine an amount of rotation of the sensed element based on detection of the varying light intensities.

10. The medication delivery device of claim 9 comprising a reservoir disposed within the device body, the reservoir including a medication.

11. A medication delivery device comprising:
a device body;
a dose setting member attached to said device body and rotatable relative to said device body about an axis of rotation during dose delivery;
a sensed element rotationally fixed with said dose setting member, said sensed element including alternating first and second surface features radially-spaced about the axis of rotation of said dose setting member, the alternating first and second surface features extending radially relative to the axis of rotation, said sensed element and said dose setting member rotating relative to said dose body during dose delivery in relation to an amount of dose delivered;
a rotation sensor including a light source emitting sensing light in a sensing direction during dose delivery, and a light sensor positioned to receive the sensing light emitted in the sensing direction during dose delivery, wherein in response to rotation of said sensed element during dose delivery the alternating first and second surface features are positioned in a path of the sensing light to vary light intensities detected by the light sensor, wherein one of the light source and the light sensor is disposed proximal to the other of the light source and the light sensor, and the alternating first and second surface features are disposed axially between the light source and the light sensor in a radially overlapping arrangement; and
an electronics assembly responsive to the rotation sensor to determine an amount of rotation of the sensed element based on detection of the varying light intensities,
wherein said alternating first and second surface features of said sensed element includes radially-inward extending projections, and the rotation sensor is extended radially outward to radially overlap with the radially-inward extending projections.

12. A medication delivery device comprising:
a device body;

a dose setting member attached to said device body and rotatable relative to said device body about an axis of rotation during dose delivery;

a sensed element rotationally fixed with said dose setting member, said sensed element including alternating first and second surface features radially-spaced about the axis of rotation of said dose setting member, said sensed element and said dose setting member rotating relative to said device body during dose delivery in relation to an amount of dose delivered, in which the surface features comprise alternating radially-directed projections and recesses;

a rotation sensor including a light source emitting sensing light in an axial direction during dose delivery, and a light sensor positioned to receive the sensing light during dose delivery, wherein the light source and the light sensor are axially disposed relative to one another, wherein in response to rotation of said sensed element during dose delivery the alternating first and second surface features are positioned to reflect the sensing light from the light source to the light sensor to vary light intensities detected by the light sensor; and an electronics assembly responsive to the rotation sensor to determine the amount of rotation of the sensed element based on detection of the varying light intensities.

13. The medication delivery device of claim 12, wherein the radially-directed projections extend radially inwardly, and the light source and light sensor extend radially outward.

\* \* \* \* \*